United States Patent [19]

Bergfeld et al.

[11] Patent Number: 5,536,849
[45] Date of Patent: Jul. 16, 1996

[54] PROCESS FOR PRODUCING GAMMA-BUTYROLACTONE

[75] Inventors: Manfred Bergfeld, Erlenbach-Mechenhard; Günter Wiesgickl, Dinkelsbühl, both of Germany

[73] Assignee: Akzo Nobel N.V., Arnhem, Netherlands

[21] Appl. No.: 283,180

[22] Filed: Aug. 3, 1994

[30] Foreign Application Priority Data

Aug. 10, 1993 [DE] Germany ............ 43 26 692.4

[51] Int. Cl.$^6$ ............ C07D 307/20; C07D 307/33
[52] U.S. Cl. ............ 549/325; 502/244
[58] Field of Search ............ 549/325

[56] References Cited

U.S. PATENT DOCUMENTS

| | | |
|---|---|---|
| 3,065,243 | 11/1962 | Dunlop et al. . |
| 3,948,805 | 4/1976 | Michalczyk et al. . |
| 4,006,165 | 2/1977 | Michalczyk et al. . |
| 4,855,273 | 8/1989 | Pohl et al. . |
| 4,935,556 | 6/1990 | Pohl et al. . |
| 5,055,599 | 10/1991 | Budge . |
| 5,118,821 | 6/1992 | Dallons et al. ............ 549/325 |
| 5,217,937 | 6/1993 | Schneider et al. . |
| 5,294,583 | 3/1994 | Pohl et al. . |

FOREIGN PATENT DOCUMENTS

| | | |
|---|---|---|
| 840452 | 4/1970 | Canada . |
| 0184055 | 6/1986 | European Pat. Off. . |
| 0404408 | 12/1990 | European Pat. Off. . |
| 2404493 | 8/1974 | Germany . |
| 2339343 | 3/1975 | Germany . |
| 3706658 | 9/1988 | Germany . |
| 3942064 | 4/1991 | Germany . |
| 4000692 | 7/1991 | Germany . |
| 3933661 | 11/1991 | Germany . |
| 4037729 | 6/1992 | Germany . |
| 49-9463 | 3/1974 | Japan ............ 549/325 |
| 673640 | 7/1979 | U.S.S.R. . |
| 1022969 | 6/1983 | U.S.S.R. . |
| 1766258 | 9/1992 | U.S.S.R. . |
| 931685 | 7/1963 | United Kingdom . |

*Primary Examiner*—Joseph E. Evans
*Attorney, Agent, or Firm*—Oliff & Berridge

[57] ABSTRACT

Gamma-butyrolactone is produced by catalytic hydrogenation of maleic anhydride in the vapor phase in the presence of copper chromite based catalysts in reduced form. The reaction is carried out using a substantially uniform catalyst derived substantially from the three components cupric oxide, chromic oxide, and silicon dioxide. The ratio of CuO to $Cr_2O_3$ to $SiO_2$ is preferably about 78:20:2. It can prove advantageous to use an inert gas such as nitrogen as a diluent.

8 Claims, No Drawings

PROCESS FOR PRODUCING GAMMA-BUTYROLACTONE

BACKGROUND

The invention relates to a process for producing gamma-butyrolactone by catalytic hydrogenation of maleic anhydride in the vapor phase.

Gamma-butyrolactone is an important chemical, significant as a starting substance for numerous syntheses. It plays a role, for example, in producing butyric acid and its derivatives, butanediol, tetrahydrofurane, N-methylpyrrolidone, polyvinylpyrrolidone, methionine, and the like. Furthermore, gamma-butyrolactone is an important solvent for acrylates and polymers with a styrene basis, among others. It can also be used as a solvent in producing synthetic fibers, for example.

A number of production processes start from maleic anhydride or derivatives such as maleic acid, succinic anhydride, or maleic ester, which are subjected to hydrogenation. The hydrogenation is usually conducted in the vapor phase and in the presence of catalysts. The patent literature describes numerous catalysts for these reactions. For example, in U.S. Pat. No. 3,065,243, a process is disclosed in which copper chromite serves as a catalyst. From the description and the examples in this patent, this conversion also produces considerable amounts of succinic anhydride, which must be recirculated.

There has been no lack of attempts to develop catalysts to improve yield and selectivity. Another aim of the studies was to extend the useful life of the catalysts, since for many catalysts the useful life is too short for continuous operation; in continuous operation, the deactivation of the catalyst, usually by coking of the catalyst, is too rapid.

In Canadian Patent 840,452, enhanced catalysts are described which have copper/zinc as a basis. These can be processed together with asbestos to form corresponding catalyst particles. The catalyst claimed in this Canadian patent, as well as the copper chromite/asbestos catalyst produced in similar fashion, do not fulfill all requirements imposed on a good catalyst for the production of gamma-butyrolactone.

In the published application DE 24 04 493, a process is described in which hydrogenation is carried out in the presence of water vapor. This is intended to reduce coking of the catalyst. One of the disadvantages of this process is that water is not an inert compound, i.e., it is a reaction component and, thus, part of the equilibrium.

Other catalysts of copper chromite basis are described in U.S. Pat. No. 4,006,165, for example, wherein this catalyst must also contain nickel. These catalysts can either be deposited on aluminum oxide or silicas such as kieselguhr, or produced by mixing with these substances.

Although numerous catalysts have been described for conversion of hydrogen and maleic anhydride to gamma-butyrolactone, there is still the need for catalysts with which this conversion can be carried out in an improved and more advantageous manner.

SUMMARY OF THE INVENTION

An object of the invention, therefore, is to provide a process for producing gamma-butyrolactone by hydrogenation of maleic anhydride in the vapor phase in the presence of a catalyst, whereby said process provides high yields, has an outstanding selectivity, can proceed at overpressure as well as at normal pressure or partial vacuum, is economical, is flexible, offers particular advantages in the further processing of the reaction product and in the recirculation of certain components, and can be conducted such that recycling of succinic acid, which arises as an intermediate product, is not necessary.

DESCRIPTION OF PREFERRED EMBODIMENTS

This object is met by a process for producing gamma-butyrolactone by catalytic hydrogenation of maleic anhydride in the vapor phase in the presence of catalysts of copper chromite basis in reduced form, characterized by carrying out the reaction using a substantially uniform catalyst derived substantially from the three components cupric oxide, chromic oxide, and silicon dioxide. Preferably, a catalyst having a basis of 68–85% by weight CuO, 15–30% by weight $Cr_2O_3$ and 0.5–5% $SiO_2$ is used, whereby these quantities relate to the catalyst before preparatory reduction. In a particularly advantageous embodiment, the ratio of CuO to $Cr_2O_3$ to $SiO_2$ is about 78:20:2.

In a particularly advantageous embodiment of the process according to the invention, hydrogenation is conducted in the presence of an inert gas as a diluent, preferably nitrogen. In addition to nitrogen, the known noble gases such as argon, krypton, helium, or mixtures either among themselves or with nitrogen can be used. Of course, the catalyst based on the three components is reduced before use in the reaction, in a conventional manner known per se. Preferably, the reduction is carried out in the reactor itself.

The reduction can be conducted according to the following procedure, for example. The catalyst, existing as a catalyst bed, is heated in the reactor in a nitrogen stream to 150° C. At this temperature, hydrogen is slowly added until an input concentration of at most 8% by volume is reached. The temperature of the catalyst bed should rise by no more than 25° C.

After the reaction heat has dissipated, the hydrogen concentration is increased to 80–100% by diminishing the nitrogen stream, and the temperature is raised to as high as 280° C. The temperature is maintained for 12 hours under $H_2$ flow; this process is usually called a post-reaction.

Of course, the reduction can take place in other ways, for example as disclosed in U.S. Pat. No. 3,065,243 at column 2, lines 54 to 66.

Production of the uniform catalyst on the basis of the three components can occur as follows. Copper and chromium in the form of dissolved salts are mixed with an appropriate soluble silicon compound, preferably in an aqueous system. The silicon compound can be water-glass or silica sol, for example. In a suitable manner, such as by alkalizing, copper, chromium and silicon can be jointly precipitated in the form of the corresponding oxides or hydroxides, producing a uniform precipitate with a homogeneous structure. After filtering and washing the precipitate, it is dried, if necessary, and then calcined. The calcined masses are appropriately comminuted and sorted as necessary according to grain size, for example by straining through multiple sieves.

A uniform catalyst within the scope of the invention is one in which the three components from which the catalyst is derived are joined homogeneously, such as is the case when the three components are precipitated jointly from a solution or when the three components are jointly melted and allowed to solidify. This, therefore, excludes coarse-grained mixtures of the individual components in which the individual components still exist as discrete particles. Conventional copper chromite catalysts on silica carriers also are not included among the catalysts according to the invention. Of course, the catalyst according to the invention can be deposited on carriers.

The catalyst can then immediately be entered into the reactor and, after appropriate reduction, used for the reaction.

The hydrogenation of maleic anhydride, i.e., the reaction of maleic anhydride with hydrogen, is conducted in the vapor phase, i.e., at elevated temperatures in the range from about 100°–400° C., for example, preferably the range from about 250°–280° C.

The maleic anhydride in vapor form can itself be introduced into the reaction space by heating and converting to the vapor phase, with appropriate dosing. It is also possible, however, to transport the required quantities of maleic anhydride vapors together with the dosed hydrogen stream. Of course, this can also occur via the inert gas such as nitrogen, if used.

The molar ratio of maleic anhydride to hydrogen can vary over large ranges in the stream of the starting substances and can be, for example, from 1:20 to 1:250, with the range 1:50 to 1:150 being preferred.

The reaction can take place at normal pressure as well as under partial vacuum or overpressure, for example between 0.1 and 10 bar.

Within the scope of the invention, an inert gas is one that does not participate in the conversion as a reaction partner or reaction product and also is itself not modified by a reaction.

By using an inert gas as a diluent, it is possible to influence the reaction favorably. The fraction of inert gas—preferably including nitrogen but also including one of the known noble gases such as helium, argon, krypton, or xenon, whereby mixtures of the noble gases or mixtures of nitrogen and noble gases can be used—can also vary over a wide range. Of course, the dilution, which depends on the other selected reaction conditions, becomes limited when the fraction of diluent is so large that too little hydrogen is present and the yield with respect to maleic anhydride decreases sharply. This limit can be determined by a few simple tests, which can be performed by one of ordinary skill in the art.

It is possible to influence the reaction by varying many of the process parameters. For example, the retention time can be changed, not only by setting different dosing rates but also by extending the reaction path, for example by using a longer reaction tube, which is filled appropriately with catalyst.

The reaction can be controlled such that the succinic anhydride produced as an intermediate step is no longer present at the end of the reactor and thus need no longer be recycled. On the other hand, if necessary, the reaction can be controlled such that succinic anhydride is still present in varyingly large amounts in the emerging reaction products and is then either processed individually after separation or is recycled in the reaction.

Surprisingly, using the catalyst according to the invention results in a high selectivity as well as a high yield. The advantages of the catalyst used in accordance with the invention are evident not only when working with or without diluent but also when the molar ratios of the reaction partners are changed or the temperature is varied. This catalyst therefore offers significant advantages, under a wide variety of process conditions, for producing gamma-butyrolactone by reduction of maleic anhydride using hydrogen.

To document the unexpectedly superior mode of reaction of the catalyst according to the invention, nine different catalysts having a basis of copper chromite are produced, wherein Catalyst No. 4 corresponds to the invention and the remaining catalysts are conventional, known copper chromite catalysts. The catalysts are derived by precipitating from corresponding solutions. The compositions of the catalysts used are given in Table 1, wherein the compositions are those prior to reduction.

TABLE 1

| Composition (before reduction) | Cat. No. |
|---|---|
| 2 CuO * $Cr_2O_3$ | 1 |
| Cu chromite (9.7% BaO) | 2 |
| 80% CuO, 20% $Cr_2O_3$ | 3 |
| 78% CuO, 20% $Cr_2O_3$, 2% $SiO_2$ | 4 |
| 42% CuO, 38% $Cr_2O_3$ | 5 |
| 33% CuO, 38% $Cr_2O_3$, 9% BaO | 6 |
| 76% CuO, 24% $Cr_2O_3$ | 7 |
| 72% CuO, 18% $Cr_2O_3$* | 8 |
| 66% CuO, 25% $Cr_2O_3$** | 9 |

*Commercial product: E-113 T, Mallinckrodt
**Commercial product: T-4421, Süd-Chemie The reduction is conducted using the following, per se conventional process:

The catalyst bed, already present in the reactor to be employed, is heated in a nitrogen stream to 150° C. At this temperature, hydrogen is slowly added until an input concentration of at most 8% by volume is reached. The temperature increase of the bulk material should not exceed 25° C. (reduction step).

After the reaction heat dissipates, the hydrogen concentration is increased to 80 to 100% and the temperature is raised to as high as 280° C. The temperature is maintained for 12 hours under $H_2$ flow (post-reduction).

The uniform catalysts are produced as follow:

EMBODIMENT A

The catalyst pellets from the reduction process are comminuted, and a fraction of 0.8 to 1.2 mm is selected. This fraction is placed in a quartz glass tube of 1 cm inside diameter and 30 cm length, heatable by silicone oil. After the reduction step, the test is conducted.

Hydrogen is dosed via a mass flow governor, and the partial pressure of the maleic anhydride is adjusted via a so-called saturator. This is accomplished by conducting hydrogen, and possibly nitrogen, through the saturator, which contains liquid maleic anhydride, whereby a known maleic anhydride partial pressure is established based on the precisely adjusted temperature. The mixture is fed to the reactor through heated lines. The reaction temperature is 275° C.

EMBODIMENT B

This embodiment is produced by a process analogous to that of embodiment A. The difference is merely that the reactor (i.e., the quartz glass tube) has an inside diameter of 3 cm and the pellets are inserted in their original size, i.e., not comminuted (diameter approx. 3 to 3.2 mm). The reaction temperature is 255°–275°.

EMBODIMENT C

Uncomminuted pellets (see B) are used. The reactor is made of high-grade steel; the dimensions are 3 cm inside diameter and 1.2 m length. Heating is via a double shell using silicone oil, whereby the temperature of the silicone oil is set equal to the reaction temperature in the embodiments (i.e., 260°–270° C.). The dosing of hydrogen and nitrogen is performed using a mass flow governor. Shortly before addition to the reactor, mixing with recycle gas takes place, which is reintroduced to the reactor after separation of the liquid products. At the same time, however, a certain fraction of the recycle gas is diverted from the system to prevent enrichment of side products in gaseous form. Liquid maleic anhydride is fed directly to the reaction via heated lines; the first 20 cm of the reactor serves as a vaporization zone filled with quartz glass wool. The catalyst is located beyond this zone.

TEST EXAMPLES WITH EMBODIMENT A

EXAMPLE A-1

The catalysts are reduced as explained above. In each case, 20 ml bulk volume is placed into the reactor and brought to a reaction temperature of 275° C. at a flow of 0.38 mol $N_2$/h and 2 mol $H_2$/h. The gas mixture is then fed via the saturator and a mole stream of maleic anhydride of 0.02 mol/h established. After 2 hours reaction time, the product mixture is analyzed. The results are given in Table 2, which follows.

TABLE 2

| Cat. No. | Yields (in %) Gamma-butyro-lactone | Yields (in %) Succinic anhydride | Conversion (in %) Maleic anhydride |
|---|---|---|---|
| 1 | 22.1 | 77.6 | 100 |
| 2 | 49.8 | 49.6 | 100 |
| 3 | 64.9 | 34.2 | 100 |
| 4 | 98.1 | — | 100 |
| 5 | 25.0 | 62 | 100 |
| 6 | 4.7 | 14.0 | 19.5 |
| 7 | 90.9 | 6.9 | 100 |

The special quality of Catalyst No. 4 is evident, and it is especially significant that the intermediate product, succinic anhydride, is completely converted. Otherwise, technical problems with the crystallization of the succinic anhydride can be expected, resulting in congestion of tubing, etc.

EXAMPLE A-2

The two tests described below are conducted exclusively with Catalyst No. 4, under conditions which are intended to illustrate the advantage of using an inert gas. Ten ml of the catalyst is placed into the reactor. The maleic anhydride stream is 0.01 mol/h. The total mole stream is 1.20 mol/h. Table 3 shows the different conditions and results. The maleic anhydride conversion is 100% in each case.

TABLE 3

| $N_2$ (mol/h) | $H_2$ (mol/h) | Yield GBL (%) | Yield SA (%) | T (°C.) |
|---|---|---|---|---|
| 0.00 | 1.19 | 97.0 | — | 275 |
| 0.19 | 1.00 | 97.5 | — | 275 |
| 0.49 | 0.70 | 98.7 | — | 275 |
| 0,69 | 0.50 | 87.0 | 11.7 | 275 |

That is, although at 275° C. no succinic anhydride (SA) is formed in the first three cases, the selectivity and consequently the yield of gamma-butyrolactone (GBL) increases with higher inert fraction.

If the inert fraction is too high (see final example in Table 3), however, not all of the intermediate product succinic anhydride is hydrogenated to gamma-butyrolactone. Therefore, only a certain inert fraction is optimal.

TEST EXAMPLES WITH EMBODIMENT B

EXAMPLE B.1

Since Catalysts Nos. 3 and 4 have a very similar composition—except for the $SiO_2$ fraction—the following comparative tests are conducted. In no case is nitrogen added. The catalyst amount is 200 g in each case, and the first 10 cm of the bulk material is diluted with 100 g of quartz glass balls having 1 mm diameter. The maleic anhydride (MA) conversion is always 100%.

The following examples in Table 4 demonstrate that the hydrogenation activity of Catalyst No. 4 is much higher than that of Catalyst No. 3, i.e., even the slight $SiO_2$ fraction leads to significantly reduced succinic anhydride formation, something which has considerable technical significance.

TABLE 4

| Cat. No. | $H_2$ (mol/h) | MA (mol/h) | T (°C.) | Yield GBL (%) | Yield SA (%) | Example No. |
|---|---|---|---|---|---|---|
| 3 | 15.8 | 0.158 | 270 | 85.7 | 11.0 | 1B |
| 4 | 15.8 | 0.158 | 270 | 85.3 | 0.1 | 2B |
| 3 | 7.87 | 0.105 | 255 | 91.2 | 5.5 | 3B |
| 4 | 7.87 | 0.105 | 255 | 92.5 | 2.0 | 4B |
| 3 | 7.87 | 0.105 | 260 | 89.5 | 6.8 | 5B |
| 4 | 7.87 | 0.105 | 260 | 90.5 | 0.7 | 6B |
| 3 | 15.75 | 0.21 | 270 | 82.8 | 14.3 | 7B |
| 4 | 15.75 | 0.21 | 270 | 91.6 | 1.3 | 8B |
| 3 | 7.87 | 0.105 | 275 | 85.6 | 0.6 | 9B |

Complete succinic anhydride conversion can result from increasing the reaction temperature for Catalyst No. 3, but at the expense of a considerable reduction in selectivity (see Example No. 9B).

In comparing Example Nos. 4B and 9B, for a similar succinic anhydride yield, a considerably higher selectivity and yield of gamma-butyrolactone can be obtained at a lower temperature with a catalyst produced according to the invention.

TEST EXAMPLES WITH EMBODIMENT C

EXAMPLE C.1

In the tests summarized in Table 5, the extremely favorable influence of added inert gas on the gamma-butyrolactone yield, particularly in pressure tests, is demonstrated using Catalyst No. 4 only.

TABLE 5

| MA pressure (bar) | Total pressure (bar) | T (°C.) | Cat. amount (g) | $N_2$ fraction (%) | Retention time (sec) | GBL yield (%) |
|---|---|---|---|---|---|---|
| 0.1188 | 6 | 270 | 360 | 0 | 2.69 | 41 |
| 0.1188 | 6 | 270 | 360 | 62 | 2.69 | 86 |
| 0.1131 | 6 | 270 | 625 | 46 | 3.14 | 92 |

TABLE 5-continued

| MA pressure (bar) | Total pressure (bar) | T (°C.) | Cat. amount (g) | $N_2$ fraction (%) | Retention time (sec) | GBL yield (%) |
|---|---|---|---|---|---|---|
| 0.1188 | 6 | 260 | 360 | 0 | 2.74 | 67 |
| 0.1188 | 6 | 260 | 360 | 30 | 2.74 | 83 |

C.2. Comparative Tests Under Pressure

The technical superiority of Catalyst No. 4 when working under pressure is again shown in comparative tests with commercially available catalysts such as Catalyst No. 8 (see Table 6). Most important are the gamma-butyrolactone yields, as well as the corresponding selectivities and residual amounts of the intermediate product succinic anhydride.

TABLE 6

| MA cat. press. (bar) | Total press. (bar) | T (°C.) | Cat. amt. (g) | $N_2$ fract. (%) | Retent. time (sec) | GBL yield (%) | SA yield (%) | No. |
|---|---|---|---|---|---|---|---|---|
| 0.116 | 6 | 270 | 630 | 0 | 2.69 | 69 | 3.1 | 8 |
| 0.116 | 6 | 270 | 630 | 0 | 2.69 | 75 | 0.2 | 4 |
| 0.116 | 6 | 270 | 630 | 50 | 2.69 | 81 | 13.0 | 8 |
| 0.116 | 6 | 270 | 630 | 50 | 2.69 | 89 | 1.5 | 4 |

The test results show that the catalyst according to the invention unexpectedly differs from the other catalysts, when working with and without diluents, at different temperatures, and at normal or overpressure.

It is clear that the reaction can be additionally controlled by selection of reaction conditions such as the ratio of the starting substances, retention time, temperature, and the like. The most favorable conditions in each case can be determined by some simple preliminary tests, which lie within the capabilities of a person of ordinary skill in the art.

What is claimed is:

1. A process for producing gamma-butyrolactone comprising catalytic hydrogenation of maleic anhydride in a vapor phase in the presence of a substantially uniform catalyst comprising copper chromite in a reduced form derived from a substantially homogeneous combination of cupric oxide, chromic oxide and silicon dioxide.

2. The process according to claim 1, wherein said combination consists essentially of cupric oxide, chromic oxide and silicon dioxide.

3. The process according to claim 1, wherein said combination comprises 68–85% by weight CuO, 15–30% by weight $Cr_2O_3$ and 0.5–5% $SiO_2$, prior to preparatory reduction of the catalyst.

4. The process according to claim 3, wherein the ratio of CuO to $Cr_2O_3$ to $SiO_2$ is about 78:20:2.

5. The process according to claim 1, wherein said hydrogenation is conducted in the presence of an inert gas.

6. The process according to claim 5, wherein said inert gas is nitrogen.

7. The process according to claim 1, wherein said reduction and said catalytic hydrogenation occur in a single reactor.

8. The process according to claim 1, wherein said maleic anhydride and hydrogen are used in a molar ratio of from 1:50 to 1:150.

* * * * *